United States Patent [19]

Koshiishi et al.

[11] Patent Number: 5,132,095

[45] Date of Patent: Jul. 21, 1992

[54] OPTICAL SENSOR

[75] Inventors: Kiyozou Koshiishi, Sagamihara; Etsuo Shinohara, Hachioji; Masatsugu Shimomura, Koganei, all of Japan

[73] Assignee: Olympus Optical Co., Ltd., Tokyo, Japan

[21] Appl. No.: 589,492

[22] Filed: Sep. 27, 1990

[30] Foreign Application Priority Data

Oct. 4, 1989 [JP] Japan ................. 1-259611

[51] Int. Cl.$^5$ .................... G01N 21/00; G01N 21/76
[52] U.S. Cl. ................. 422/82.07; 422/82.08; 422/82.01; 422/52; 422/82.09
[58] Field of Search ............ 422/82.07, 82.08, 82.09, 422/82.11, 82.06, 82.01, 52; 128/633, 634, 636; 350/96.12, 96.29

[56] References Cited

U.S. PATENT DOCUMENTS

| | | | |
|---|---|---|---|
| 4,695,122 | 9/1987 | Ishida et al. | 350/96.12 |
| 4,712,865 | 12/1987 | Hsu et al. | 350/96.29 |
| 4,752,115 | 6/1988 | Murray, Jr. et al. | 128/634 |
| 4,762,799 | 8/1988 | Seitz et al. | 422/82.07 |
| 4,852,967 | 8/1989 | Cook et al. | 350/96.29 |
| 4,871,221 | 10/1989 | Imoto | 350/96.29 |
| 4,929,561 | 5/1990 | Hirschfeld | 422/82.07 |
| 4,992,385 | 2/1991 | Godfrey | 422/82.11 |

FOREIGN PATENT DOCUMENTS 61-241656 10/1986 Japan.
61-254634 11/1986 Japan.

OTHER PUBLICATIONS

J. Membrane Biol. 19, pp. 1–36 (1974).
Kagaku (Science) vol. 55, No. 5 (1985), pp. 290–299.
Ann. NY. Acad. Sci., vol. 33, pp. 217–241 (1977).
Denki Kagaku No. 12 (1985), pp. 942–946.
J. Am. Chem. Soc. 1988, 110, pp. 571–577.
Bunshi Sekkei Gijutsu (Molecular Designing Technique) pp. 89–101.

Primary Examiner—Robert J. Warden
Assistant Examiner—T. A. Trembley
Attorney, Agent, or Firm—Frishauf, Holtz, Goodman & Woodward

[57] ABSTRACT

An optical sensor for detecting a specific substance in a solution, based on optical changes, includes a substrate and a thin membrane formed on the substrate. The membrane is formed of an ion complex material of an ionic amphipathic compound with a polymer having ionic groups of the opposite electrical charge, a potential-sensitive dye and a substance-selective compound.

24 Claims, 2 Drawing Sheets

OPTICAL SENSOR

BACKGROUND OF THE INVENTION

1. Field of the Invention

The present invention relates to an optical sensor for detecting a specific component such as ions in a sample by an optical change due to a potential-sensitive dye which is fixed in an ultra-thin membrane. It also relates to a specific substance detecting device comprising such an optical sensor. The sensor of the present invention is referred to as an optical sensor, since it detects a specific substance based on optical changes.

2. Description of the Related Art

The detection of a biopotential by using a potential-sensitive dye has been successfully developed, and its usefulness has been demonstrated, as described in J. Membrane Biol., vol. 19, pages 1–36 (1974), and Kagaku (Science) vol. 55, No. 5 (1985), pages 290–299. The former document, FIG. 4 on page 15, shows the result of experiments in which potential-sensitive dyes are diffused into a living cell, tissue, or the like, and proves that there is a linear relationship, within a certain range, between change in membrane potential and optical change of absorbance or fluorescence. Numerous kinds of dyes are known as potential-sensitive dyes and many examples are listed in the former document, pages 28–33.

However, these dyes do not have a function of identifying or selecting a specific substance such as an ion, and are sensitive only to a potential. Since each type of dye has its own response speed, sensitivity, durability, and the like, the most suitable one should be selected for a particular purpose. Further, as described in Ann. NY. Acad. Sci., vol. 33, page 217–241 (1977), Table 2 on page 223 in particular, the sensitivities of these dyes are all about $1 \times 10^5$ V/cm, and are effective, in fact, only in a thin membrane of the submicron order, such as a cell membrane.

Since preparation of an ultra-thin membrane, as mentioned above, under moderate conditions has up to now been extremely difficult, use of the above potential-sensitive dyes are limited mainly to studies of biomembrane functions. The only exception to this is Published Unexamined Japanese Patent Application (PUJPA) No. 61-241656, which discloses an electrolyte concentration measuring sensor. This sensor comprises a polymer layer in which ion-selective substances are dispersed, and a potential-sensitive dye fixed on the surface of the polymer layer. The fluorescent intensity varies in accordance with changes in ion concentration in a sample solution. According to the technique stated in this PUJPA, the layer or film is basically prepared by a coating method, and it is extremely difficult to prepare a minute or dense ultra-thin membrane which is free from defects. Consequently, a sensor made with such a membrane may be ineffective in terms of sensitivity and response speed.

In the meantime, the Langmuir-Blodgett (LB) film-/membrane preparation technique has been developed, allowing a variety of thin membranes to be designed. The LB membrane preparation technique is explained in detail in Bunshi Sekkei Gijutsu (Molecular Designing Technique) edited by Masakazu OKADA et al. (published by Science Forum Co., Ltd, Japan), pages 89 to 101. An amphipathic or amphiphilic substance is used as the material for the LB membrane. Stearic acid, ω-tricosenic acid, and the like, generally used as materials for forming the LB membrane, have carboxyl groups. These carboxyl groups are ionically dissociated to have a negative charge in an aqueous solution. It has been found by the present inventors that when an LB membrane is made of these carboxylic acids and the potential-sensitive dyes are embedded therein, ionic components in a sample solution and the negatively-charged carboxylate ions bring about non-specific coupling and dissociation therefrom, thereby creating a problem in terms of sensitivity and stability.

SUMMARY OF THE INVENTION

Therefore, it is an object of the present invention to provide an optical sensor and a specific substance detecting device for detecting a specific component or substance in a sample, based on an optical change due to a potential-sensitive dye, by fixing the dye within a ultra-thin membrane.

According to the present invention, there is provided an optical sensor comprising a substrate; and a thin membrane formed on the substrate and comprising an ion complex material of an ionic amphipathic compound with a polymer having ionic groups of the opposite electrical charge, a potential-sensitive dye and molecule(s) having a substance-selective function.

The substrate may be a silicon thin plate coated with a metal oxide or metal nitride. The thin membrane can also be formed on an exposed core portion of an optical waveguide (optical fiber) having a core transmitting an exciting radiation or an incident light therethrough, and a cladding layer surrounding the core and confining the radiation within the core. The exposed core portion can be made by removing a part of the cladding layer at its end portion.

Further, a specific substance detecting device of the present invention can be provided by combining the optical sensor of the invention with means for irradiating a light having a constant wavelength to the optical sensor, and means for detecting optical changes occurring due to the light-irradiated dye.

The light irradiating means may be the one which irradiates an exciting radiation of a constant wavelength for the potential-sensitive dye, and the optical change detecting means may be the one which measures change in fluorescence generated by the irradiated dye. Alternatively, the light irradiating means may be the one which projects a light of a constant wavelength onto the optical sensor, and the optical change detecting means may be the one which measure change in absorbance of the potential-sensitive dye.

DETAILED DESCRIPTION OF THE PREFERRED EMBODIMENTS

Figure 1:
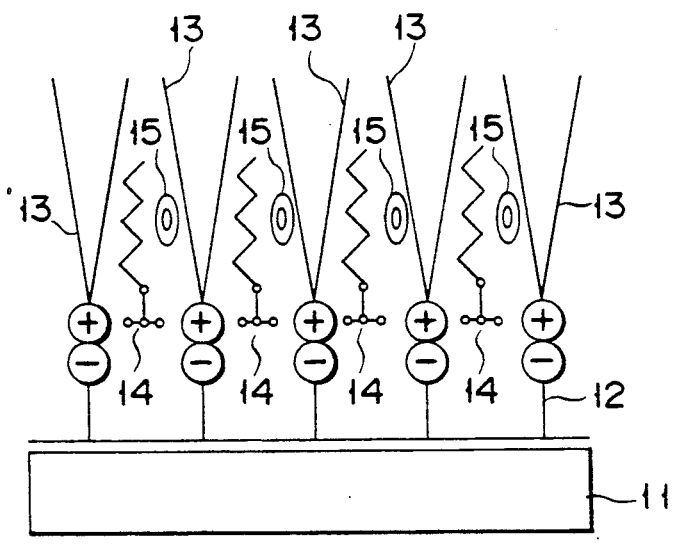
FIG. 1 is a schematic view of a structure of an optical sensor according to one embodiment of the present invention.

The present invention is described in more detail below.

The inventors of the present invention investigated the possibility of overcoming the prior art problems regarding the materials of LB membranes for enclosing and fixing potential-sensitive dyes therein, focusing on the organic thin membrane disclosed in Published Unexamined Japanese Patent Application (PUJPA) No. 61-254634. This PUJPA discloses a method of preparing an LB membrane by forming an ion complex on a water surface from a cationic ammonium salt and an anionic water-soluble polymer. In this case, since the obtained ion complex LB membrane is electrically neutral, it rarely gives rise to a non-specific reaction with ions in a sample solution to be measured. Finally, the present inventors came to a conclusion that an ionic amphipathic or amphiphilic compound and a polymer containing an ionic group having an electrical charge opposite to the ionic amphipathic compound should be used as a material for an ultra-thin membrane which can advantageously enclose or embed a potential-sensitive dye therein. Further, it has been found that, in preparing an ultra-thin membrane by the LB technique using the above-noted material, when a molecule or compound having a substance-selective function (for example, ion selectivity) is present together with the potential-sensitive dye, a desired optical sensor can be obtained.

In the present invention, all of the ionic amphipathic compounds and the ionic polymers having the opposite electric charge, as well as the preparation technique, disclosed in PUJPA No. 61-25634 can be utilized to prepare the LB membrane of the invention.

The amphipathic compound is either cationic or anionic. Representative amphipathic compounds are quaternary ammonium salts and phosphate ester salts and the like, preferably having two long chain alkyl groups. Preferred examples of the amphipathic compound are dimethyldioctylammonium bromide, dimethyldioctadecylammonium bromide represented by

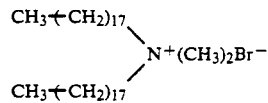

and sodium dihexadecyl phosphate represented by

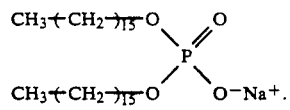

The ionic polymer should be anionic when the amphipathic compound used is cationic, and should be cationic when the amphipathic compound used is anionic, to form a substantially neutral ion complex. Representative water-soluble polymers are those having carboxylic groups, carboxylate salt groups, sulfate salt groups, sulfonate salt groups, quaternary ammonium salt groups, or pyridinium salt groups. Preferred anionic polymers include polymers represented by the formula:

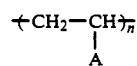

where A is $-SO_3^-Na^+$, $-OSO_3^-Me^+$, or

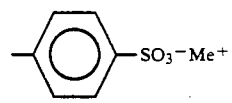

and Me is $Na^+$ or $K^+$. The polymers include sodium polyvinyl sulfonate, sodium or potassium polyvinyl sulfate and sodium or potassium polystyrene sulfonate. Also preferred are sodium carboxymethyl cellulose, cellulose sulfate sodium salt, dextran sulfate sodium salt, and chondroitin sulfate sodium salt. Sodium carboxymethyl cellulose and potassium polyvinyl sulfate are particularly preferred.

Preferred cationic polymers include poly (vinylpyridine hydrohalide), poly(N-ethylvinylpyridinium bromide), poly(allylamine hydrohalide), linear polyethyleneimine hydrohalide represented by

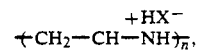

and poly(lysine hydrohalide) represented by

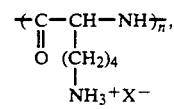

where X is a halogen atom. Poly(4-vinylpyridine hydrohalide) is particularly preferable.

Preferable combinations of the amphipathic compound with the ionic polymer include: dimethyldioctylammonium bromide or dimethyldioctadecylammonium bromide with sodium carboxymethyl cellulose or potassium polyvinyl sulfate; and sodium dihexadecyl phosphate with poly(4-vinylpyridine hydrohalide).

Meanwhile, examples of the potential-sensitive dye which can be used in the present invention include potential-sensitive cyanine dyes, merocyanine dyes, rhodamine dyes, oxonol dyes, and styryl dyes which are disclosed in J. Membrane Biol., vol. 19, pages 1-36 (1974), the disclosure of which is hereby incorporated by reference. Preferred dyes are those represented by the following formulas:

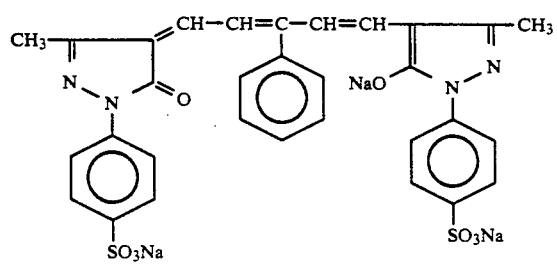

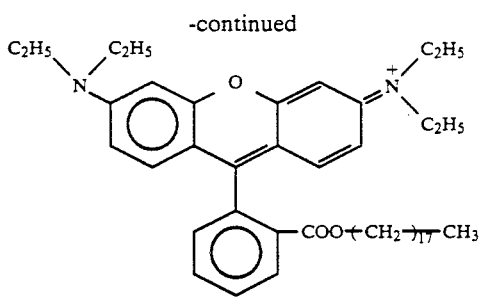

Examples of molecules or compounds having a substance-selective function or ion-selectivity which can be used are valinomycin, crown ethers such as

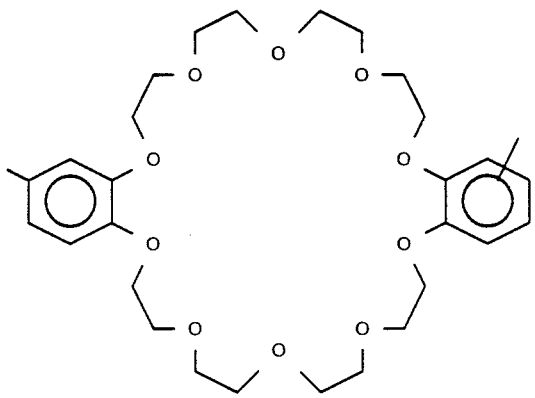

and cryptands such as

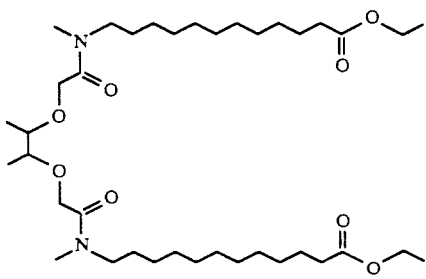

which are described in Denki Kagaku (Electrochemistry) vol. 53, No. 12, pages 942-946, (1985), as well as spherands such as

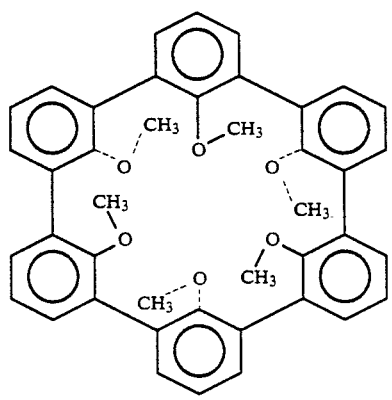

which are described in J. Am. Chem. Soc,. vol. 110, No. 2, pages 571-577 (1988). These molecules have the ion-selectivity of selecting a specific ion such as potassium, calcium, sodium, lithium, or magnesium ion.

In order to form a desired LB membrane on a substrate using the ionic amphipathic compound, the water-soluble ionic polymer, the potential-sensitive dye and the substance-selective compound, a solution of the amphipathic compound, potential-sensitive dye and substance-selective compound in an organic solvent is spread on the surface of an aqueous solution containing the ionic polymer dissolved therein. The spread layer is compressed to a predetermined surface pressure, the substrate is dipped in, and withdrawn from, the aqueous solution, while maintaining the surface pressure. The amphipathic compound in the spread layer and the ionic polymer in the aqueous solution form an ion complex at the interface, which is transferred to the substrate with the potential-sensitive dye and the substance-selective compound dispersed and enclosed therein, forming a desired LB membrane.

The water-soluble ionic polymer may be used at a concentration of 0.01 to 10% by weight in the aqueous solution. The amphipathic compound may be used in an amount of 0.0001 to 50% by weight with respect to the ionic polymer. The potential-sensitive dye and the substance-selective compound may be used in amounts of 0,2 to 10% by weight, and 1 to 80% by weight, respectively, with respect to the ion complex.

FIG. 1 shows a schematic view of an example of the LB membrane. As shown in this figure, a water-soluble polymer 12 having the negative charge (anionic) are aligned on a hydrophilic substrate 11 such as quartz glass with its anionic groups being arranged upward, and a cationic amphipathic compound 13 such as quaternary ammonium salt 13 is aligned on the water-soluble polymer 12 with its cations (quaternary nitrogen) facing the anionic groups, thereby forming an ion complex. Potential-sensitive dyes 14 and ion-selective molecules 15 such as valinomycin are dispersed and fixed the ion complex LB membrane.

The substrate, which supports the LB membrane, does not have to be of quartz glass shown in FIG. 1. It may be a silicon thin plate whose surface is covered with a metal oxide (hydrophilic) such as silicon oxide, tantalum oxide, aluminum oxide, and the like, or a silicon thin plate whose surface is covered with silicon nitride (hydrophobic). Silicon can be protected from contaminants such as an alkali metal or the like by covering the surface thereof with silicon oxide, silicon nitride, or the like, using a conventional technique (CVD, sputtering, and the like) in the field of semiconductors. In this manner, both types of substrates, i.e. those with the hydrophilic and hydrophobic surfaces, can be easily produced in great quantities. In addition, hydrophilic surfaces can be prepared by using a silane coupling agent.

Figure 2:
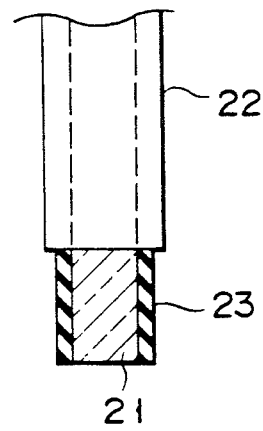
FIG. 2 shows another optical sensor according to the present invention.

Further, as shown in FIG. 2, an exposed core potion of an optical waveguide (optical fiber) having a core 21 and a cladding layer 22 confining a light can provide the substrate. The exposed core portion can be provided by removing the portion of the cladding layer 22 at its one end portion. An LB membrane 23 is formed on the exposed core. The LB membrane can be formed on the end face of the core.

The LB membrane can be a single monomolecular layer as shown in FIG. 1. Alternatively it can be a multilayer in which a plurality of monomolecular layers are stacked within a thickness range that the sensitivity is not greatly decreased. The total thickness of the LB membrane should preferably be about 30 Å-1 μm.

The molecules in the LB membrane which have the substance-selective function such as valinomycin selects specific ions in an aqueous sample solution. The potential-sensitive dyes in the LB membrane senses a potential which is unique to the selected particular ions. Upon radiation of light (excitation light having a constant wave length and incident light having a constant wave length), the potential-sensed dyes bring about the potential changes in fluorescence or absorbance in accordance with the potential value. By measuring this optical change, the concentration of specific ions in a sample solution can be measured.

Figure 3:
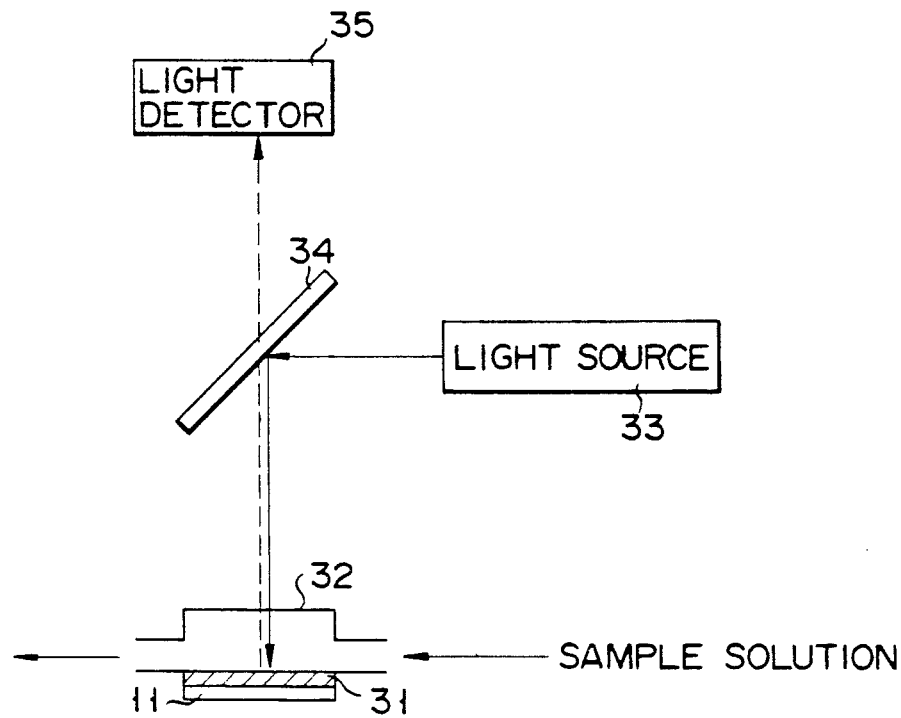
FIGS. 3 and 4 illustrate specific substance detecting device according to different embodiments of the invention.

FIG. 3 shows a specific substance detecting device of the invention. This device has a flow cell 32 incorporating therein an optical sensor consisting of a substrate 11 on which an LB membrane (shown at 31) as shown in FIG. 1. A light (such as G exciting line) from a light source 33 such as a mercury lamp is projected onto the LB membrane 31 via a dichroic mirror 34. The potential-sensitive dyes in the LB membrane 31 emits fluorescence, the intensity of which corresponds to the concentration of specific ions such as potassium ions present in a sample solution flowing in the flow cell 32. Of the light from the LB membrane 31, the excitation light is removed or reflected by the dichroic mirror 34, and only the fluorescent light passes the mirror 34, which is detected by a photodetector 35 such as photomultiplier.

Figure 4:
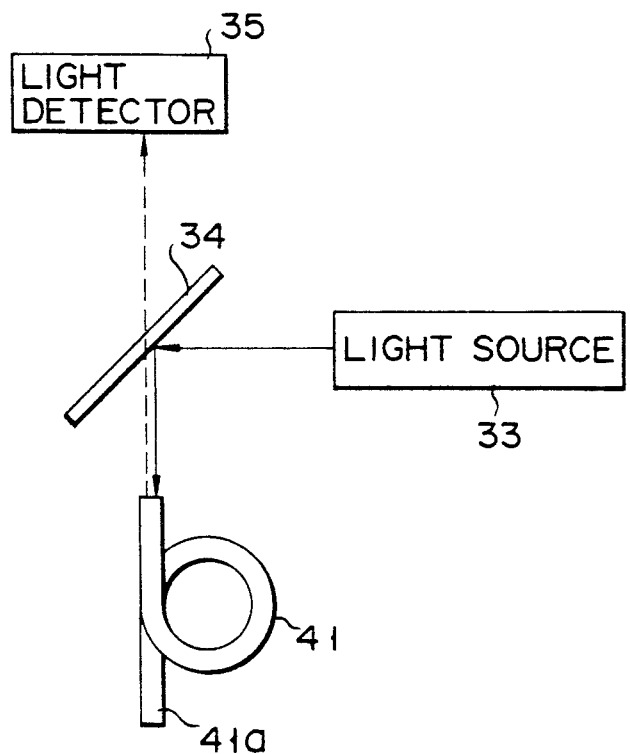

FIG. 4 shows another detecting device similar to that of FIG. 3 except for an optical fiber 41 used in place of the flow cell. A portion of the cladding layer at the tip end portion 41a of the optical fiber 41 is removed, and an LB membrane is formed on the exposed core surface, as described with reference to FIG. 2. The LB membrane is allowed to contact with a sample solution. The light is transmitted through the optical fiber.

The present invention will be explained in further detail with reference to the following examples.

EXAMPLE 1

A trough was filled with an aqueous solution of sodium carboxymethyl cellulose at the concentration of 10 mg/l water. 10 μl of a chloroform solution in which dimethyldioctylammonium bromide (10 mg/10 cc), octadecylrhodamine B (1 mg/10 cc) and valinomycin (1 mg/10 cc) were dissolved, was spread on the surface of the aqueous solution. Then, it was let stand for 5 minutes. Thereafter, the spread layer was compressed at a speed of 0.4 mm/sec until the surface pressure thereof became 30 mN/cm, and a desired monomolecular LB membrane was formed on a quartz glass substrate while maintaining the surface pressure constant. Thus, an optical sensor was prepared. Since valinomycin has a highly selective property toward potassium ions, this sensor serves as a potassium ion sensor.

EXAMPLE 2

A specific substance detecting device as shown in FIG. 3 was fabricated. The optical sensor prepared in Example 1 was incorporated in the flow cell 32, and a photomultiplier was used as the light detector 35. G exciting line (540 nm) from the mercury lamp 33 is projected onto the LB membrane 31 via the dichroic mirror 34. A potential-sensitive pigment in LB membrane 31 emits fluorescence (620 nm), the intensity of which corresponds to the concentration of Potassium ions present in the sample solution flowing in flow cell 32. The excitation light is removed by the dichroic mirror 34, and the intensity of fluorescence is detected by the photomultiplier 35.

EXAMPLE 3

A specific substance detecting device as shown in FIG. 4 was prepared. The optical fiber used had a core of $F_2$ glass and a cladding layer of BK 7 glass. The cladding portion of the tip end portion of the optical fiber 41 was removed, and an LB membrane was formed on the exposed core surface, as shown in FIG. 2. This LB membrane was formed using the technique of Example 1. The LB membrane is brought into contact with a sample solution. The fluorescence of which intensity corresponds to the concentration of potassium ions present in the sample solution transmits through the optical fiber, and is detected by the photomultiplier 35.

The present invention has been explained with respect to the specific embodiments described above. The present invention should not be limited thereto. For example, the systems in which fluorescence of the potential-sensitive dye is detected has been described, but systems in which the absorbance of the potential-sensitive dye is detected is also within the scope of the present invention.

As described above, the present invention provides an optical sensor and a specific substance detecting device for detecting specific substances at a high sensitivity with a good response based on an optical change due to the potential-sensitive dye which is fixed in an ultra-thin membrane.

What is claimed is:

1. A specific substance sensing element comprising:
   a substrate; and
   a membrane formed on said substrate and comprising an ion complex material of an ionic amphipathic compound with a polymer having ionic groups of the opposite electrical charge, a potential-sensitive dye and a compound having a substance-selective function.

2. The specific substance sensing element according to claim 1, wherein said substrate is a silicon thin plate covered with a metal oxide or metal nitride.

3. The specific substance sensing element according to claim 1, wherein said membrane is formed on an exposed core surface formed by removing a part of a cladding layer of an optical waveguide comprising a core and the cladding layer.

4. The specific substance sensing element according to claim 1, wherein said membrane has a total thickness of about 30 Å to 1 μm.

5. The specific substance sensing element according to claim 1, wherein said dye is present in an amount of about 0.2 to 10% by weight based on the weight of the ion complex material.

6. The specific substance sensing element according to claim 1, wherein said substance-selective compound is present in an amount of about 1 to 80% by weight based on the weight of the ion complex material.

7. A specific substance detecting device comprising
   A specific substance sensing element according to claim 1;
   first means for irradiating a light having a constant wavelength to the optical sensor whereby irradiating said potential-sensitive dye; and second means for detecting optical changes occurring due the light-irradiated dye.

8. The device according to claim 7, wherein said first means irradiates exciting light having a constant wave length to the sensor, and said second means measures a change in intensity of fluorescence emitted from the potential-sensitive dye due to the exciting light.

9. The device according to claim 7, wherein said first means projects light having a constant wave length onto the sensor, and said second means measures change in absorbance of the potential-sensitive dye.

10. The device according to claim 7 wherein for the optical sensor, the ion complex material comprises (a) dimethyldioctylammonium bromide or dimethyloctadecylammonium bromide with sodium carboxymethyl cellulose or potassium polyvinyl sulfate, or (b) sodium dihexadecyl phosphate with poly (4-vinylpyridine hydrohalide); the potential-sensitive dye is selected from the group consisting of cyanine dyes, merocyanine dyes, rhodamine dyes, oxonol dyes and styryl dyes; the compound having a substance-selective function is selected from the group consisting of valinomycin, crown ethers, cryptands and spherands; the ionic amphipathic compound is present in an amount of 0.0001 to 50% by weight with respect to the ionic polymer; the dye is present in an amount of 0.2 to 10% by weight with respect to the ion complex material; and substance-selective compound is present in an amount of 1 to 80% by weight with respect to the weight of the ion complex material.

11. The device according to claim 10, wherein the dye is selected from the group consisting of

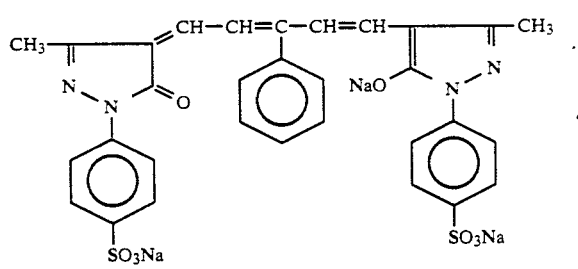

and

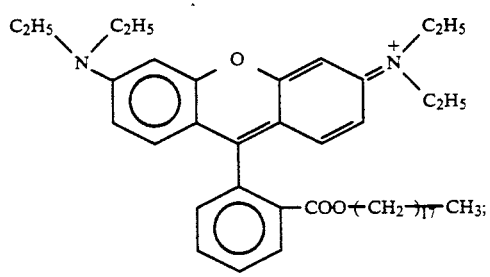

and the compound having a substance-selective function is selected from the group consisting of a crown ether of the formula

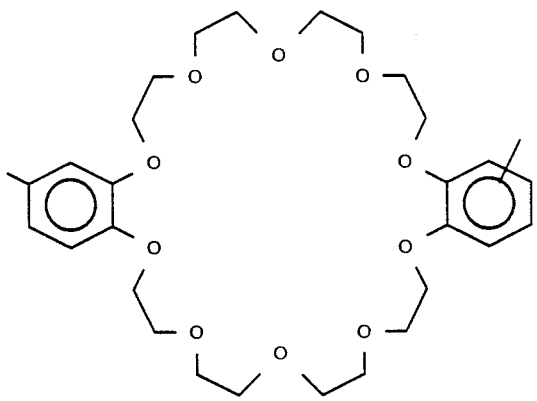

a cryptand of the formula

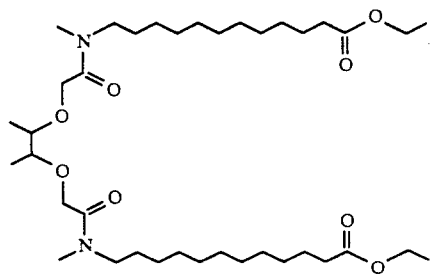

and a spherand of the formula

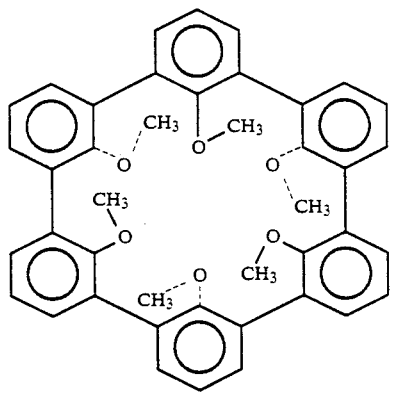

12. The sensor according to claim 1, wherein the ionic complex material comprises said polymer and a compound selected from the group consisting of quaternary ammonium salts and phosphate ester salts.

13. The sensor according to claim 1, wherein the ionic complex material comprises said polymer and a compound selected from the group consisting of dimethyldioctylammonium bromide, dimethyldioctadecylammonium bromide of the formula

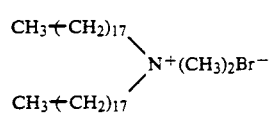

and sodium dihexadecyl phosphate of the formula

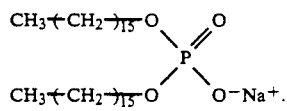

14. The sensor according to claim 1, wherein the polymer is selected from the group consisting of sodium polyvinyl sulfonate, sodium polyvinyl sulfate, potassium polyvinyl sulfate, sodium polystyrene sulfonate, potassium polystyrene sulfonate, sodium carboxymethyl cellulose, cellulose sulfate sodium salt, dextran sulfate sodium salt, chrondroitin sulfate sodium salt, poly(vinylpyridine hydrohalide), poly(N-ethylvinylpyridinium bromide), poly(allylamine hydrohalide), linear polyethyleneimine hydrohalide of the formula

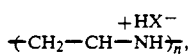

wherein X is a halogen atom and poly(lysine hydrohalide) of the formula

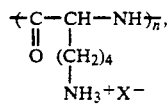

wherein X is a halogen atom.

15. The sensor according to claim 1, wherein the ionic complex material comprises (a) dimethyldioctylammonium bromide or dimethyldioctadecylammonium bromide with sodium carboxymethyl cellulose or potassium polyvinyl sulfate; or (b) sodium dihexadecyl phosphate with poly(4-vinylpyridine hydrohalide).

16. The sensor according to claim 15, wherein the potential-sensitive dye is selected from the group consisting of potential-sensitive cyanine dyes, merocyanine dyes, rhodamine dyes, oxonol dyes and styryl dyes.

17. The sensor according to claim 16, wherein the compound having a substance-selective function is selected from the group consisting of valinomycin, crown ethers, cryptands and spherands.

18. The sensor according to claim 17, wherein the ionic amphipathic compound is present in an amount of 0.0001 to 50% by weight with respect to the ionic polymer; the dye is present in an amount of 0.2 to 10% by weight with respect to the ion complex material; and the substance-selective compound is present in an amount of 1 to 80% by weight with respect to the weight of the ion complex material.

19. The sensor according to claim 16, wherein the compound having a substance-selective function is selected from the group consisting of a crown ether of the formula

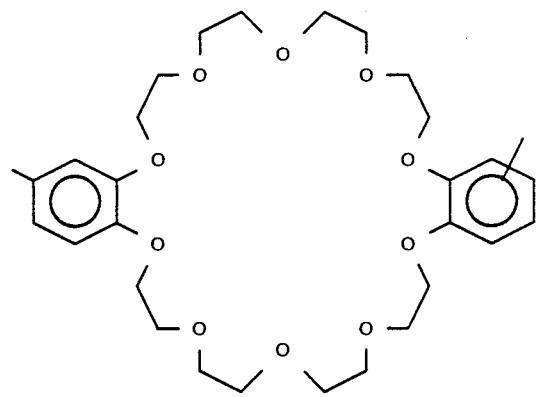

a cryptand of the formula

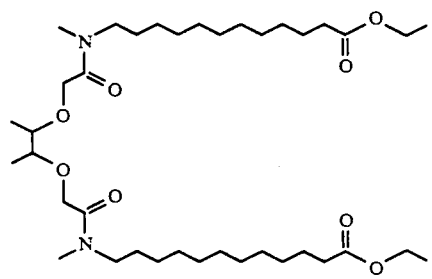

and a spherand of the formula

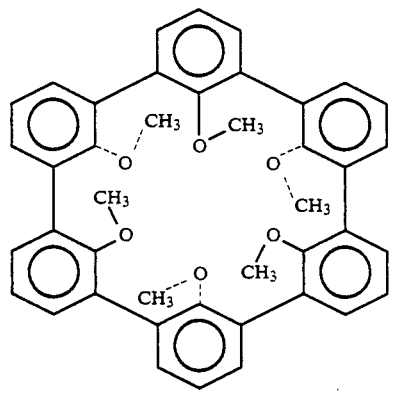

20. The sensor according to claim 15, wherein the dye is selected from the group consisting of

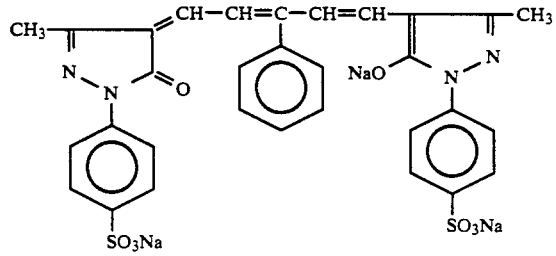

and

-continued

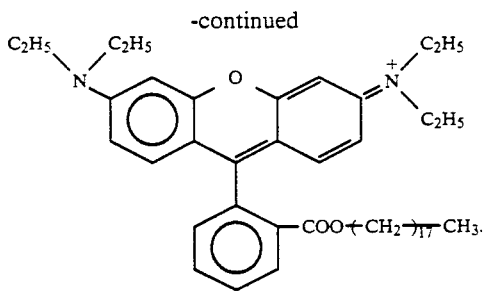

21. A specific substance sensing element for detecting specific ions in an aqueous solution based on optical changes, comprising:
   a substrate; and
   a membrane supported on said substrate and comprising an ion complex formed between an ionic amphipatic compound and a water-soluble polymer having an ionic group of a polarity opposite to said amphiphilic compound, said membrane having, dispersed and enclosed therein, an ion-selective compound and a potential-sensitive compound which emits fluorescence, the intensity of which corresponds to the concentration of ions selected by said ion-selective compound.

22. An ion detecting device comprising:
   A specific substance sensing element according to claim 21;
   first means for irradiating an exciting light which excites the potential-sensitive dye to emit fluorescence therefrom; and
   second means for measuring the intensity of said fluorescence.

23. The device according to claim 22, wherein for the optical sensor, the ion complex comprises (a) dimethyldioctylammonium bromide or dimethyloctadecylammonium bromide with sodium carboxymethyl cellulose or potassium polyvinyl sulfate, or (b) sodium dihexadecyl phosphate with poly (4-vinylpyridine hydrohalide); the potential-sensitive dye is selected from the group consisting of cyanine dyes, merocyanine dyes, rhodamine dyes, oxonol dyes and styryl dyes; the compound having a substance-selective function is selected from the group consisting of valinomycin, crown ethers, cryptands and spherands; the ionic amphipathic compound is present in an amount of 0.0001 to 50% by weight with respect to the ionic polymer; the dye is present in an amount of 0.2 to 10% by weight with respect to the ion complex; and substance-selective compound is present in an amount of 1 to 80% by weight with respect to the weight of the ion complex.

24. The optical according to claim 21, wherein the ion complex material comprises (a) dimethyldioctylammonium bromide or dimethyloctadecylammonium bromide with sodium carboxymethyl cellulose or potassium polyvinyl sulfate, or (b) sodium dihexadecyl phosphate with poly (4-vinylpyridine hydrohalide); the potential-sensitive dye is selected from the group consisting of cyanine dyes, merocyanine dyes, rhodamine dyes, oxonol dyes and styryl dyes; the compound having a substance-selective function is selected from the group consisting of valinomycin, crown ethers, cryptands and spherands; the ionic amphipathic compound is present in an amount of 0.0001 to 50% by weight with respect to the ionic polymer; the dye is present in an amount of 0.2 to 10% by weight with respect to the ion complex material; and substance-selective compound is present in an amount of 1 to 80% by weight with respect to the weight of the ion complex material.

* * * * *